US011096559B2

(12) United States Patent
Kitano

(10) Patent No.: US 11,096,559 B2
(45) Date of Patent: Aug. 24, 2021

(54) ENDOSCOPE AND ENDOSCOPE APPARATUS

(71) Applicant: FUJIFILM Corporation, Tokyo (JP)

(72) Inventor: Ryo Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 514 days.

(21) Appl. No.: 15/973,531

(22) Filed: May 8, 2018

(65) Prior Publication Data

US 2018/0344132 A1 Dec. 6, 2018

(30) Foreign Application Priority Data

May 31, 2017 (JP) .............................. JP2017-108460

(51) Int. Cl.
*A61B 1/00* (2006.01)
*A61B 1/06* (2006.01)
*A61B 1/05* (2006.01)

(52) U.S. Cl.
CPC ...... *A61B 1/00096* (2013.01); *A61B 1/00006* (2013.01); *A61B 1/0011* (2013.01); *A61B 1/051* (2013.01); *A61B 1/06* (2013.01)

(58) Field of Classification Search
CPC ... A61B 1/00096; A61B 1/008; A61B 1/0011; A61B 1/0051; A61B 1/05; G02B 23/2407; G02B 23/2423; G02B 23/243; G02B 23/2446; G02B 23/2476; H04N 5/2253; H05K 1/111; H05K 1/14; H05K 2201/1028; H05K 2201/1031; H05K 2201/10977; H01L 2224/73253
See application file for complete search history.

(56) References Cited

U.S. PATENT DOCUMENTS

| | | | | |
|---|---|---|---|---|
| 4,832,003 A | * | 5/1989 | Yabe ...................... | A61B 1/051 348/65 |
| 5,554,100 A | * | 9/1996 | Leiner ................. | A61B 1/00179 385/117 |
| 2002/0186478 A1 | * | 12/2002 | Watanabe ................ | G02B 7/02 359/819 |
| 2006/0006239 A1 | * | 1/2006 | Tanaka ................. | H04N 5/2253 235/472.01 |
| 2010/0022841 A1 | * | 1/2010 | Takahashi .............. | G02B 7/025 600/162 |

(Continued)

FOREIGN PATENT DOCUMENTS

JP 2016137231 8/2016

*Primary Examiner* — Matthew J Kasztejna
(74) *Attorney, Agent, or Firm* — JCIPRNET

(57) ABSTRACT

There are provided an endoscope in which adhesion strength between two optical members can be enhanced and an endoscope apparatus including the endoscope. An endoscope includes an insertion part that is to be inserted into a subject, a first unit that is built in a distal end portion of the insertion part and includes a prism, a second unit that is built in the distal end portion and includes a cover glass, an adhesive layer that is formed between the light-emitting surface of the prism and the surface of the cover glass and adheres the prism to the cover glass, and a resin layer that fills a gap larger than the thickness of the adhesive layer formed between the first unit and the second unit. The thermal expansion coefficient of the resin layer is set to $\frac{1}{10}$ or less of the thermal expansion coefficient of the adhesive layer.

17 Claims, 5 Drawing Sheets

(56) References Cited

U.S. PATENT DOCUMENTS

| | | | | |
|---|---|---|---|---|
| 2015/0014805 A1* | 1/2015 | Yamada | ............ | H01L 27/14618 |
| | | | | 257/443 |
| 2016/0178884 A1* | 6/2016 | Hanada | .............. | G02B 27/0025 |
| | | | | 359/738 |
| 2017/0322411 A1* | 11/2017 | Igarashi | .............. | G02B 23/2484 |
| 2018/0168046 A1* | 6/2018 | Miyawaki | .......... | G02B 23/2484 |
| 2019/0116300 A1* | 4/2019 | Okuno | ................. | H04N 5/2254 |

\* cited by examiner

ENDOSCOPE AND ENDOSCOPE APPARATUS

CROSS-REFERENCE TO RELATED APPLICATIONS

The present application claims priority under 35 U.S.C. § 119 to Japanese Patent Application No. 2017-108460, filed on May 31, 2017. Each of the above application(s) is hereby expressly incorporated by reference, in its entirety, into the present application.

BACKGROUND OF THE INVENTION

1. Field of the Invention

The present invention relates to an endoscope and an endoscope apparatus.

2. Description of the Related Art

An imaging module includes a semiconductor chip in which an imaging element, such as a charge coupled device (CCD) image sensor or a complementary metal oxide semiconductor (CMOS) image sensor, is formed and a circuit board on which a circuit to be electrically connected to the semiconductor chip is formed. The imaging module is used in a lot of devices, such as a digital camera, a smart phone or an endoscope.

JP2016-137231A discloses an imaging module of an endoscope in which the light incident surface of a prism and a columnar light-transmitting parallel flat plate, which is provided at an opening of the end face of a prism holder and closes the opening, are adhered to each other by an adhesive.

SUMMARY OF THE INVENTION

A plurality of components, which are mounted in the distal end portion of the endoscope and are adhered to each other by an adhesive, are disposed in a very small space and are used under an environment up to a high temperature of 100° C. or higher from a room temperature. For this reason, an influence of the thermal expansion of the adhesive, which adheres these components, needs to be considered. Further, since the distal end portion of the endoscope is often subject to a shock from the outside, an influence of such an external force is required to be also considered to enhance an adhesive force.

An influence of the thermal expansion of the adhesive and how to ensure the adhesive force between the components of the endoscope are not considered in JP2016-137231A.

The invention has been made in consideration of the above-mentioned circumstances, and an object of the invention is to provide an endoscope in which adhesion strength between two optical members can be enhanced and an endoscope apparatus including the endoscope.

An endoscope of the invention comprises an insertion part that is to be inserted into a subject, a first unit that is built in a distal end portion of the insertion part and includes a first optical member, a second unit that is built in the distal end portion of the insertion part and includes a second optical member, an adhesive layer that is formed between a light transmission surface of the first optical member and a light transmission surface of the second optical member and adheres the first optical member to the second optical member, and a resin layer that fills a gap larger than a thickness of the adhesive layer formed between the first unit and the second unit. A thermal expansion coefficient of the resin layer is set to 1/10 or less of a thermal expansion coefficient of the adhesive layer.

An endoscope apparatus of the invention comprises the endoscope, a light source device to which the endoscope is connected; and a control device to which the endoscope is connected and which controls the endoscope and the light source device.

According to the invention, it is possible to provide an endoscope in which adhesion strength between two optical members can be enhanced and an endoscope apparatus including the endoscope.

DESCRIPTION OF THE PREFERRED EMBODIMENTS

An embodiment of the invention will be described below with reference to the drawings.

Figure 1:
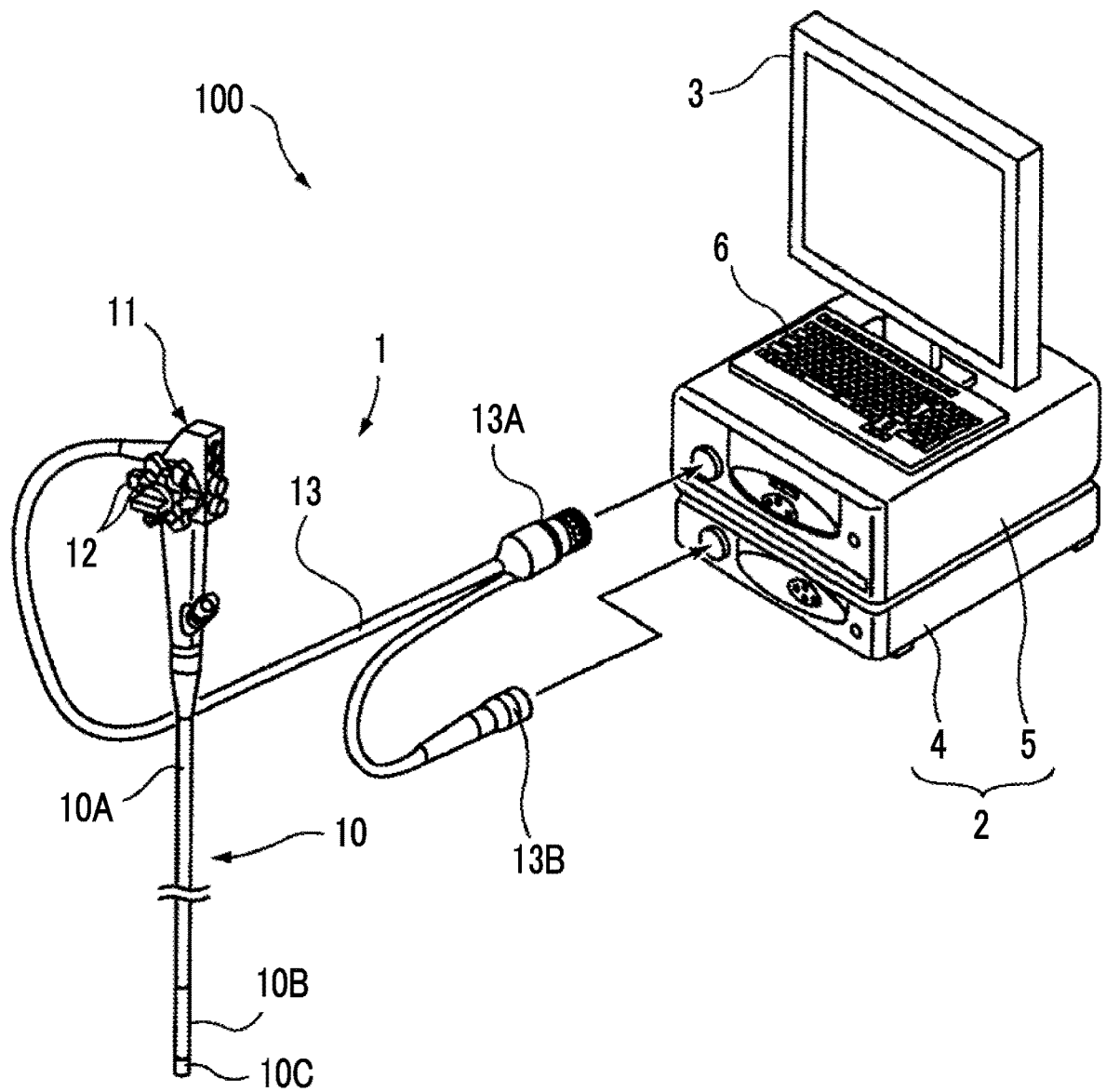
FIG. 1 is a diagram showing the schematic structure of an endoscope apparatus 100 according to an embodiment of the invention.

FIG. 1 is a diagram showing the schematic structure of an endoscope apparatus 100 according to an embodiment of the invention.

As shown in FIG. 1, the endoscope apparatus 100 includes an endoscope 1 and a body section 2 that includes a control device 4 and a light source device 5 to which the endoscope 1 is connected. The control device 4 controls the endoscope 1 and the light source device 5.

A display unit 3 that displays image information and the like and an input unit 6 that receives an input operation are connected to the control device 4.

The endoscope 1 includes: an insertion part 10 that is a tubular member extending in one direction and is to be inserted into a subject; an operation box 11 that is provided at a proximal end portion of the insertion part 10 and is provided with buttons used to perform a mode-switching operation, an imaging operation, an air/water supply operation, a suction operation, and the like; an angle knob 12 that is provided so as to be connected to the operation box 11; and a universal cord 13 that includes connector parts 13A and 13B allowing the endoscope 1 to be detachably connected to the light source device 5 and the control device 4, respectively.

Although not shown, various channels, such as a forceps channel into which a treatment tool, such as forceps, is to be inserted, channels for supplying air and water, and a channel for suction, are provided in the operation box 11 and the insertion part 10.

The insertion part 10 includes a soft portion 10A that has flexibility, a bendable portion 10B that is provided at the distal end of the soft portion 10A, and a distal end portion 10C that is provided at the distal end of the bendable portion 10B.

The bendable portion 10B is adapted to be freely bendable by an operation for rotationally moving the angle knob 12. Since the bendable portion 10B can be bent in any direction at any angle according to a region of a subject in which the endoscope 1 is to be used, the distal end portion 10C can face a desired region to be observed.

An observation window that is used to take light from a region to be observed, an illumination window that is used to emit illumination light to the region to be observed, an opening that is used to take in and out a treatment tool, such as forceps, an air/water supply nozzle, and the like are provided at the distal end of the distal end portion 10C. An imaging module 40 to be described later is disposed in the distal end portion 10C at a position facing the observation window.

Figure 2:
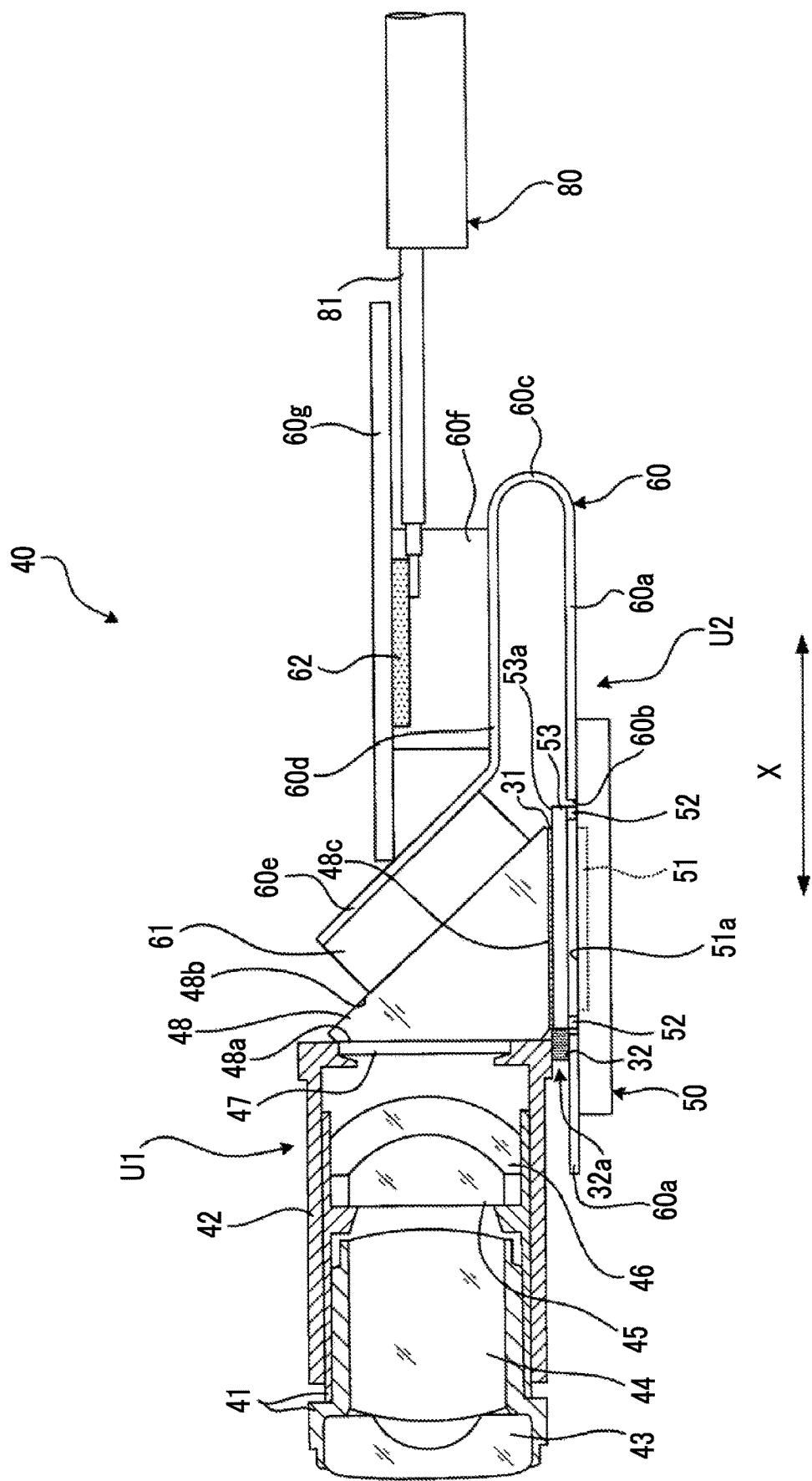
FIG. 2 is a schematic cross-sectional view showing the schematic structure of an imaging module 40 that is built in a distal end portion 10C of an endoscope 1 shown in FIG. 1.
Figure 3:
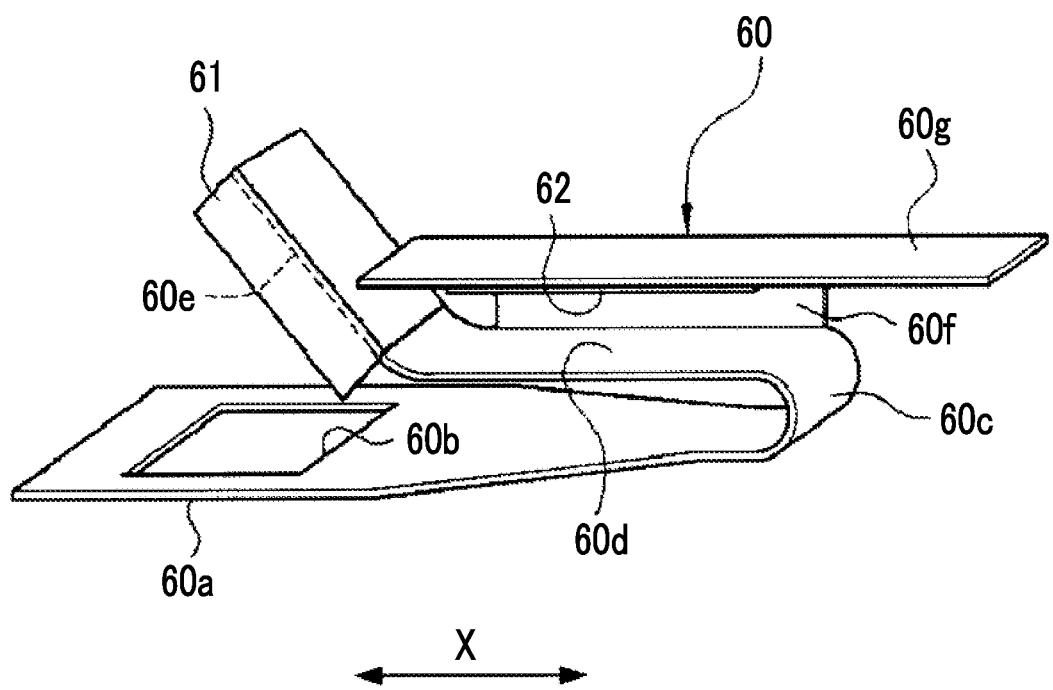
FIG. 3 is a perspective view showing the appearance of a flexible board 60 of the imaging module 40 shown in FIG. 2.

FIG. 2 is a schematic cross-sectional view showing the schematic structure of the imaging module 40 that is built in the distal end portion 10C of the endoscope 1 shown in FIG. 1. FIG. 3 is a perspective view showing the appearance of a flexible board 60 of the imaging module 40 shown in FIG. 2.

The imaging module 40 includes a first unit U1, a second unit U2, an adhesive layer 31, and a resin layer 32.

The first unit U1 includes: a lens barrel 41 that receives a first lens 43, a second lens 44, a third lens 45, and a fourth lens 46; a cylindrical prism holder 42 that is fitted to the outer periphery of the lens barrel 41; a fifth lens 47 that is formed of a columnar transparent parallel flat plate provided to face the fourth lens 46 and to close an opening of an end face of the prism holder 42 facing the bendable portion 10B; and a prism 48. The first unit U1 is a unit that receives an image-forming optical system.

The second unit U2 includes: a semiconductor chip 50 in which an imaging element 51 is formed on a board made of a semiconductor, such as silicon; and a flexible board 60 that is electrically connected to the semiconductor chip 50. The second unit U2 is a unit that takes an optical image formed by the image-forming optical system and converts the taken optical image into electrical signals.

The first lens 43, the second lens 44, the third lens 45, the fourth lens 46, the fifth lens 47, and the prism 48 are arranged in this order from a position, which faces the observation window of the distal end of the distal end portion 10C, in a longitudinal direction X of the insertion part 10. The fifth lens 47 forms an imaging lens.

The prism 48 is fixed to the end face of the prism holder 42, which faces the bendable portion 10B, and the light-emitting surface of the fifth lens 47, which closes the opening of this end face of the prism holder 42, by, for example, an adhesive, such as a thermosetting resin or a photocurable resin.

The prism 48 bends light, which is incident on a light incident surface 48a through an imaging lens group that includes the first lens 43, the second lens 44, the third lens 45, and the fourth lens 46 received in the lens barrel 41, and the fifth lens 47, in a direction perpendicular to the optical axis of the imaging lens group on an inclined surface 48b, and emits the light from a light-emitting surface 48c. The prism 48 forms a first optical member, the light-emitting surface 48c of the prism 48 forms the light transmission surface of the first optical member.

The flexible board 60 is a circuit board having flexibility. As shown in FIG. 3, the flexible board 60 includes one end portion 60a that has the shape of a flat plate and extends in the longitudinal direction X, a straight portion 60d that is parallel to the end portion 60a and faces a part of the end portion 60a, a bent portion 60c that connects the end portion 60a to the straight portion 60d and is bent in a U shape, the other end portion 60e that extends along the inclined surface 48b of the prism 48 to a position facing the inclined surface 48b from the end portion of the straight portion 60d in the longitudinal direction X, a branch portion 60f that protrudes from the straight portion 60d in a direction orthogonal to the longitudinal direction of the straight portion 60d and is bent at a right angle, and a sub-board 60g that is connected to the distal end of the branch portion 60f and is parallel to the straight portion 60d.

An opening portion 60b, which passes in a direction perpendicular to the light-emitting surface 48c of the prism 48, is formed at the end portion 60a of the flexible board 60.

A soldering portion 62, which is used to connect a terminal group of a circuit of the flexible board 60 to each signal line 81 of a signal cable 80 built in the insertion part 10 of the endoscope 1, is formed on the sub-board 60g.

Components, such as a circuit for driving the imaging element 51 and an amplifier for amplifying an imaging signal output from the imaging element 51, are provided on the surface of the other end portion 60e facing the prism 48. A cover 61, which is used to protect these components, is fixed to the other end portion 60e. The cover 61 is fixed to the prism 48.

The semiconductor chip 50 includes an imaging element 51, such as a CCD image sensor or a CMOS image sensor, a spacer 52 that is formed of a frame-like member formed around an imaging surface 51a on the surface of the imaging element 51 on which the imaging surface 51a is formed, and a cover glass 53 that is formed of a flat plate-like translucent member formed on the spacer 52 and parallel to the imaging surface 51a.

The semiconductor chip 50 is fixed to the surface of the end portion 60a opposite to the surface of the end portion 60a of the flexible board 60, which faces the prism 48, in a state in which the imaging surface 51a of the imaging element 51 faces the opening portion 60b of the end portion 60a of the flexible board 60. The semiconductor chip 50 is electrically connected to terminals formed on the end portion 60a.

Each of a surface 53a of the cover glass 53 and the light-emitting surface 48c of the prism 48 is formed of a flat surface parallel to the longitudinal direction X. The adhesive layer 31 made of an adhesive is formed between the surface 53a of the cover glass 53 and the light-emitting surface 48c of the prism 48. The surface 53a of the cover glass 53 and the light-emitting surface 48c of the prism 48 are adhered to each other by the adhesive layer 31.

The cover glass 53 forms a second optical member, and the surface 53a of the cover glass 53 forms the light transmission surface of the second optical member.

A gap 32a, which is larger than the thickness of the adhesive layer 31 (the thickness of the adhesive layer 31 in the direction perpendicular to the light-emitting surface 48c), is formed between the end portion of the prism holder 42, which is a component of the first unit U1, facing the bendable portion 10B and the end portion 60a of the flexible board 60 that is a component of the second unit U2.

The gap 32a is filled with the resin layer 32 that contains a resin as a main component. That is, one end portion of the resin layer 32 in the direction perpendicular to the light-emitting surface 48c is in contact with the prism holder 42, and the other end portion of the resin layer 32 in the direction perpendicular to the light-emitting surface 48c is in contact with the end portion 60a of the flexible board 60.

The resin layer 32 is provided to prevent light from starting to leak from the outer peripheral surface of the prism 48, to reinforce adhesion strength between the prism 48 and the cover glass 53, or for the purpose of both preventing light from starting to leak from the outer peripheral surface of the prism 48 and reinforcing the adhesion strength between the prism 48 and the cover glass 53. It is possible to allow the resin layer 32 to have a function to block light by making the resin layer 32 contain a coloring agent, such as oil black.

Since the gap 32a is filled with the resin layer 32, the thickness of the resin layer 32 (the thickness of the resin layer 32 in the direction perpendicular to the light-emitting surface 48c) is set to be larger than the thickness of the adhesive layer 31. The thickness of the adhesive layer 31 is set to be very small in terms of ensuring optical performance and the like, and is set to a thickness of, for example, about several μm.

The thickness of the resin layer 32 is set to be sufficiently larger than the thickness of the adhesive layer 31. Specifically, the thickness of the resin layer 32 is set to 100 or more times the thickness of the adhesive layer 31.

The thermal expansion coefficient of the resin layer 32 is set to be sufficiently lower than the thermal expansion coefficient of the adhesive layer 31 to prevent the separation of the adhesive layer 31 that occurs due to the increase of the gap 32a caused by the expansion of the resin layer 32 in a thickness direction.

In a case in which the thermal expansion coefficient of the resin layer 32 is set to $1/100$ or less of the thermal expansion coefficient of the adhesive layer 31 since the thickness of the resin layer 32 is set to 100 or more times the thickness of the adhesive layer 31 as described above, the expansion of the gap 32a can be reliably prevented and the separation of the adhesive layer 31 can be prevented.

In a case in which the thermal expansion coefficient of the adhesive layer 31 is denoted by $\alpha1$, the thickness of the adhesive layer 31 is denoted by d1, the thermal expansion coefficient of the resin layer 32 is denoted by $\alpha2$, and the thickness of the resin layer 32 is denoted by d2, it is possible to reliably prevent the expansion of the gap 32a and to prevent the separation of the adhesive layer 31 by satisfying a condition of "$\alpha1 \times d1 \geq \alpha2 \times d2$".

However, since a difference between the thickness of the resin layer 32 and the thickness of the adhesive layer 31 is very large by about 100 times, an effect of suppressing the expansion of the gap 32a is sufficiently obtained even though the thermal expansion coefficient of the resin layer 32 is set to $1/10$ or less of the thermal expansion coefficient of the adhesive layer 31. That is, it is preferable that the thermal expansion coefficient of the resin layer 32 is set to $1/10$ or less of the thermal expansion coefficient of the adhesive layer 31, and it is more preferable that the thermal expansion coefficient of the resin layer 32 is set to $1/100$ or less of the thermal expansion coefficient of the adhesive layer 31.

Specifically, in a case in which 3041N, which is a modified acrylate adhesive manufactured by Three Bond Co., Ltd., is employed as the adhesive layer 31 and EPO-TEK (registered trademark) 320, which is an epoxy resin-based adhesive manufactured by Epoxy Technology, Inc., is used as the resin layer 32, the thermal expansion coefficient of the resin layer 32 can be set to $1/10$ or less of the thermal expansion coefficient of the adhesive layer 31.

Further, in a case in which CEMEDINE (registered trademark) 1565, which is an epoxy resin-based adhesive manufactured by Cemedine Co., Ltd., is employed as the adhesive layer 31, and AT4291A, which is an epoxy resin-based adhesive manufactured by NTT Advanced Technology Corporation, is used as the resin layer 32, the thermal expansion coefficient of the resin layer 32 can be set to $1/10$ less of the thermal expansion coefficient of the adhesive layer 31.

A thermal expansion coefficient of this specification means a value measured by a method that is defined by Japanese Industrial Standards.

In the endoscope 1 having the above-mentioned structure, the thermal expansion coefficient of the resin layer 32 is set to $1/10$ or less of the thermal expansion coefficient of the adhesive layer 31. For this reason, the thermal expansion of the resin layer 32 can be prevented under a high temperature environment. As a result, it is possible to enhance the reliability of a product by preventing the separation of the adhesive layer 31.

Figure 4:
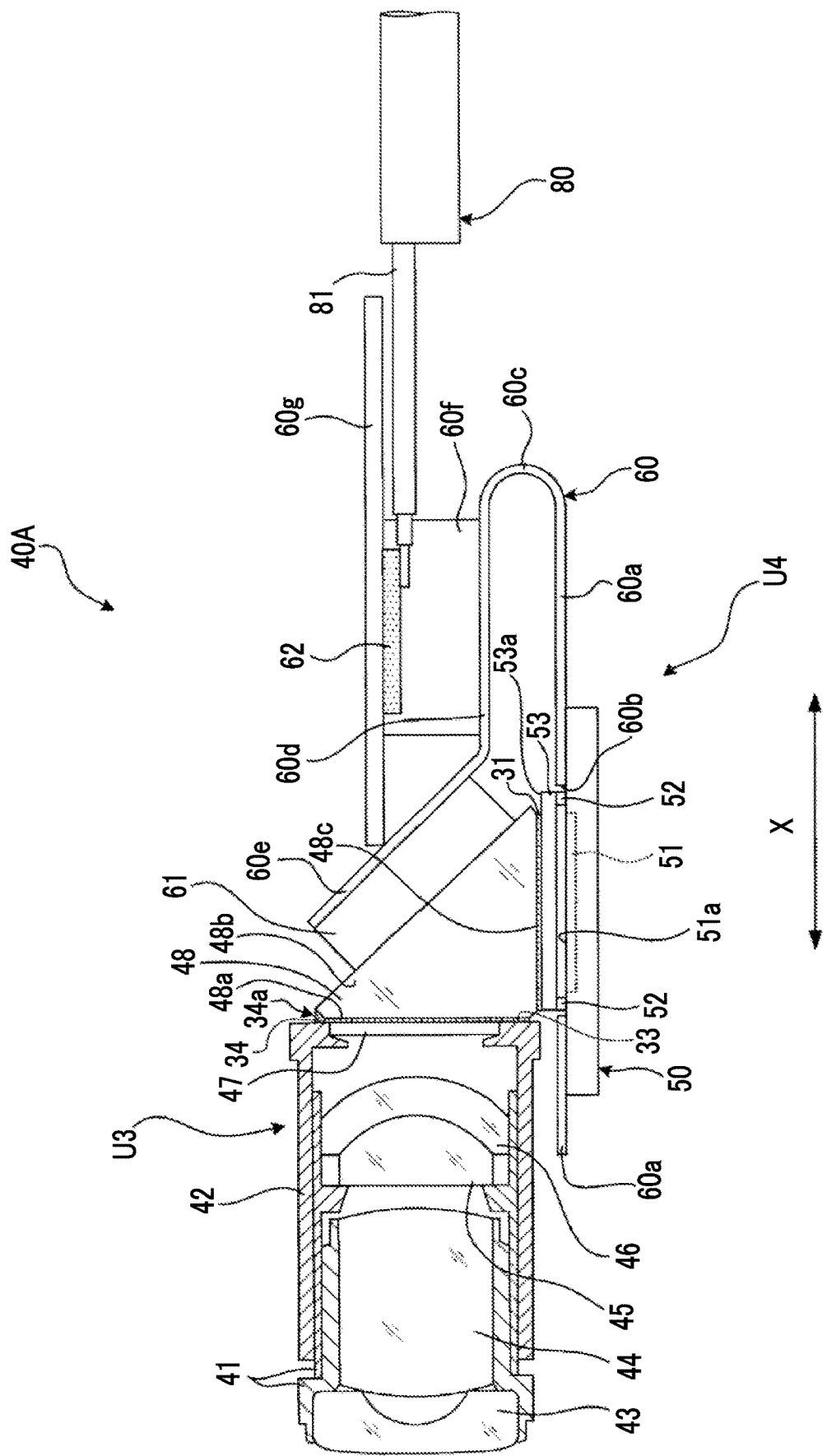
FIG. 4 is a schematic cross-sectional view of an imaging module 40A that is a modification example of the imaging module 40 shown in FIG. 2.

FIG. 4 is a schematic cross-sectional view of an imaging module 40A that is a modification example of the imaging module 40 shown in FIG. 2. The same components of FIG. 4 as those of FIG. 2 are denoted by the same reference numerals as those of FIG. 2 and the description thereof will be omitted.

The imaging module 40A has the same structure as the imaging module 40 except that the first unit U1 is changed to a first unit U3, the second unit U2 is changed to a second unit U4, an adhesive layer 33 and a resin layer 34 are added, and the resin layer 32 is omitted.

The first unit U3 includes a lens barrel 41, a prism holder 42, a first lens 43, a second lens 44, a third lens 45, a fourth lens 46, and a fifth lens 47.

The second unit U4 includes a prism 48, a semiconductor chip 50, and a flexible board 60.

Each of the light-emitting surface of the fifth lens 47 and a light incident surface 48a of the prism 48 is formed of a flat surface perpendicular to a longitudinal direction X. The adhesive layer 33 made of an adhesive is formed between the light-emitting surface of the fifth lens 47 and the light incident surface 48a of the prism 48. The light-emitting surface of the fifth lens 47 and the light incident surface 48a of the prism 48 are adhered to each other by the adhesive layer 33.

In the imaging module 40A, the fifth lens 47 forms a first optical member and the light-emitting surface of the fifth lens 47 forms the light transmission surface of the first optical member. Further, the prism 48 forms a second optical member and the light incident surface 48a of the prism 48 forms the light transmission surface of the second optical member.

A gap 34a, which is larger than the thickness of the adhesive layer 33 (the thickness of the adhesive layer 33 in the direction perpendicular to the light incident surface 48a), is formed between the end face of the prism holder 42, which is a component of the first unit U3, facing the bendable portion 10B and the prism 48 that is a component of the second unit U4.

The gap 34a is filled with the resin layer 34 that contains a resin as a main component.

The resin layer 34 is provided to prevent light from starting to leak from the outer peripheral surface of the prism 48, to reinforce adhesion strength between the prism 48 and the fifth lens 47, or for the purpose of both preventing light from starting to leak from the outer peripheral surface of the prism 48 and reinforcing the adhesion strength between the prism 48 and the fifth lens 47.

The thickness of the resin layer 34 (the thickness of the resin layer 34 in the direction perpendicular to the light incident surface 48a) is set to be larger than the thickness of the adhesive layer 33. The thickness of the adhesive layer 33 is set to be very small in terms of ensuring optical performance and the like, and is set to a thickness of, for example, about several µm.

The thickness of the resin layer 34 is set to be sufficiently larger than the thickness of the adhesive layer 33. For example, the thickness of the resin layer 34 is set to 10 or more times the thickness of the adhesive layer 33.

The thermal expansion coefficient of the resin layer 34 is set to be sufficiently lower than the thermal expansion coefficient of the adhesive layer 33 to prevent the separation of the adhesive layer 33 that occurs due to the increase of the gap 34a caused by the expansion of the resin layer 34 in a thickness direction.

Specifically, in a case in which the thermal expansion coefficient of the resin layer 34 is set to 1/10 or less of the thermal expansion coefficient of the adhesive layer 33, the expansion of the gap 34a can be reliably prevented and the separation of the adhesive layer 33 can be prevented.

In a case in which the thermal expansion coefficient of the adhesive layer 33 is denoted by $\alpha 11$, the thickness of the adhesive layer 33 is denoted by d11, the thermal expansion coefficient of the resin layer 34 is denoted by $\alpha 21$, and the thickness of the resin layer 34 is denoted by d21, it is possible to reliably prevent the expansion of the gap 34a and to prevent the separation of the adhesive layer 33 by satisfying a condition of "$\alpha 11 \times d11 \geq \alpha 21 \times d21$".

In a case in which the same layers as the adhesive layer 31 and the resin layer 32 are used as the adhesive layer 33 and the resin layer 34, the thermal expansion coefficient of the resin layer 34 can be set to 1/10 or less of the thermal expansion coefficient of the adhesive layer 33.

In an endoscope 1 on which the imaging module 40A having the above-mentioned structure is mounted, the thermal expansion coefficient of the resin layer 34 is set to 1/10 or less of the thermal expansion coefficient of the adhesive layer 33. For this reason, the thermal expansion of the resin layer 34 can be prevented under a high temperature environment. As a result, it is possible to enhance the reliability of a product by preventing the separation of the adhesive layer 33.

Figure 5:
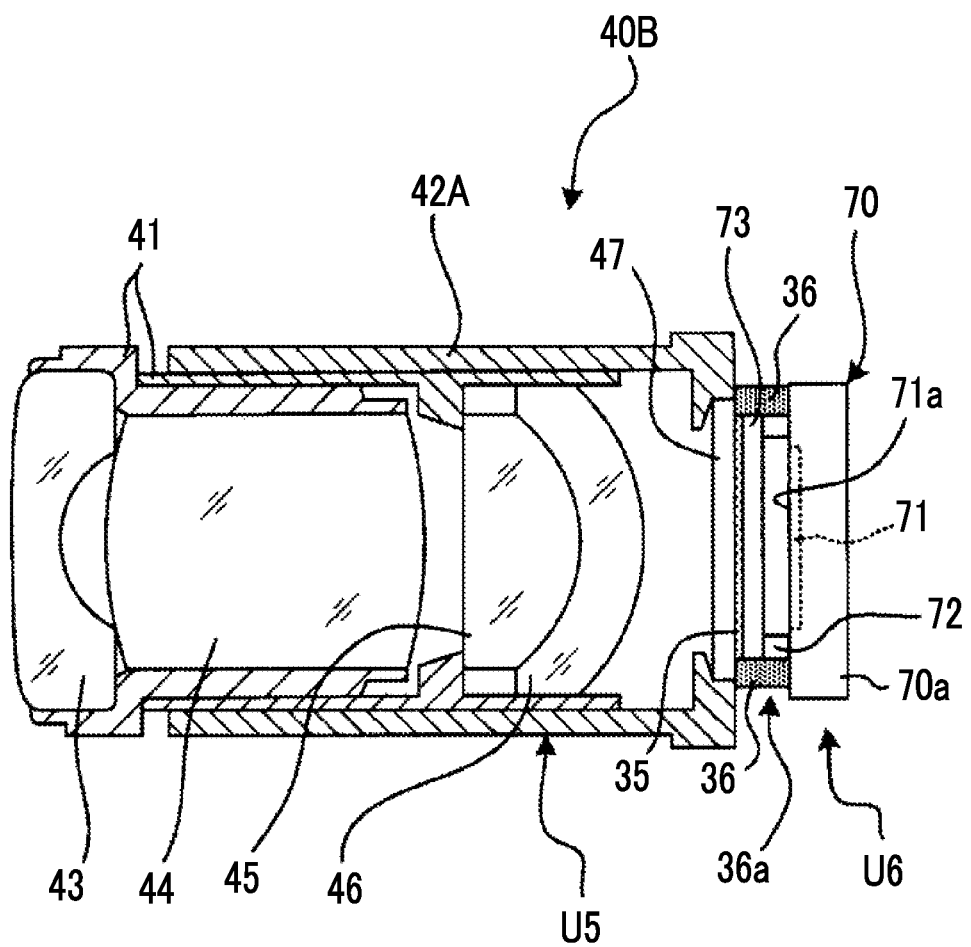
FIG. 5 is a schematic cross-sectional view of an imaging module 40B that is a modification example of the imaging module 40 shown in FIG. 2.

FIG. 5 is a schematic cross-sectional view of an imaging module 40B that is a modification example of the imaging module 40 shown in FIG. 2. The same components of FIG. 5 as those of FIG. 2 are denoted by the same reference numerals as those of FIG. 2 and the description thereof will be omitted. The circuit board connected to the imaging element and the signal cable connected to the circuit board are not shown in the imaging module 40B shown in FIG. 5.

The imaging module 40B includes a first unit U5, a second unit U6, an adhesive layer 35, and a resin layer 36.

The first unit U5 includes the lens barrel 41, the first lens 43, the second lens 44, the third lens 45, the fourth lens 46, and the fifth lens 47 of the imaging module 40 shown in FIG. 2 and a cylindrical lens holder 42A to be fitted to the lens barrel 41. The fifth lens 47 is fitted to an opening portion of the end face of the lens holder 42A facing the bendable portion 10B. The first unit U5 is a unit that receives an image-forming optical system.

The second unit U6 includes: a semiconductor chip 70 in which an imaging element 71 is formed on a board 70a made of a semiconductor, such as silicon; and a circuit board (not shown) that is electrically connected to the semiconductor chip 70. The second unit U6 is a unit that takes an optical image formed by the image-forming optical system and converts the taken optical image into electrical signals.

The semiconductor chip 70 includes an imaging element 71, such as a CCD image sensor or a CMOS image sensor, a spacer 72 that is formed of a frame-like member formed around an imaging surface 71a on the surface of the imaging element 71 on which the imaging surface 71a is formed, and a cover glass 73 that is formed of a flat plate-like translucent member formed on the spacer 72 and parallel to the imaging surface 71a.

Each of the surface of the cover glass 73 and the light-emitting surface of the fifth lens 47 is formed of a flat surface perpendicular to a longitudinal direction X of the insertion part 10 of the endoscope 1. The adhesive layer 35 made of an adhesive is formed between the surface of the cover glass 73 and the light-emitting surface of the fifth lens 47. The surface of the cover glass 73 and the light-emitting surface of the fifth lens 47 are adhered to each other by the adhesive layer 35.

In the imaging module 40B, the fifth lens 47 forms a first optical member and the light-emitting surface of the fifth lens 47 forms the light transmission surface of the first optical member. Further, the cover glass 73 forms a second optical member and the surface of the cover glass 73 forms the light transmission surface of the second optical member.

A gap 36a, which is larger than the thickness of the adhesive layer 35 (the thickness of the adhesive layer 35 in a direction parallel to the optical axis of the fifth lens 47), is formed between the end portion of the lens holder 42A, which is a component of the first unit U5, facing the bendable portion 10B and the board 70a of the semiconductor chip 70 that is a component of the second unit U6.

The gap 36a is filled with the resin layer 36 that contains a resin as a main component. The resin layer 36 is provided to reinforce adhesion strength between the fifth lens 47 and the cover glass 73.

Since the gap 36a is filled with the resin layer 36, the thickness of the resin layer 36 (the thickness of the resin layer 36 in the direction parallel to the optical axis of the fifth lens 47) is set to be larger than the thickness of the adhesive layer 35. The thickness of the adhesive layer 35 is set to be very small in terms of ensuring optical performance and the like, and is set to a thickness of, for example, about several µm.

The thickness of the resin layer 36 is set to be sufficiently larger than the thickness of the adhesive layer 35. Specifically, the thickness of the resin layer 36 is set to 100 or more times the thickness of the adhesive layer 35.

The thermal expansion coefficient of the resin layer 36 is set to be sufficiently lower than the thermal expansion coefficient of the adhesive layer 35 to prevent the separation of the adhesive layer 35 that occurs due to the increase of the gap 36a caused by the expansion of the resin layer 36 in a thickness direction.

In a case in which the thermal expansion coefficient of the resin layer 36 is set to 1/100 or less of the thermal expansion coefficient of the adhesive layer 35 since the thickness of the resin layer 36 is set to 100 or more times the thickness of the adhesive layer 35, the expansion of the gap 36a can be reliably prevented and the separation of the adhesive layer 35 can be prevented.

In a case in which the thermal expansion coefficient of the adhesive layer 35 is denoted by $\alpha 12$, the thickness of the adhesive layer 35 is denoted by d12, the thermal expansion coefficient of the resin layer 36 is denoted by $\alpha 22$, and the thickness of the resin layer 36 is denoted by d22, it is possible to reliably prevent the expansion of the gap 36a and to prevent the separation of the adhesive layer 35 by satisfying a condition of "$\alpha 12 \times d12 \geq \alpha 22 \times d22$".

However, since a difference between the thickness of the resin layer 36 and the thickness of the adhesive layer 35 is very large by about 100 times, an effect of suppressing the expansion of the gap 36a is sufficiently obtained even though the thermal expansion coefficient of the resin layer 36 is set to $1/10$ or less of the thermal expansion coefficient of the adhesive layer 35. That is, it is preferable that the thermal expansion coefficient of the resin layer 36 is set to $1/10$ or less of the thermal expansion coefficient of the adhesive layer 35, and it is more preferable that the thermal expansion coefficient of the resin layer 36 is set to $1/100$ or less of the thermal expansion coefficient of the adhesive layer 35.

Specifically, in a case in which the same layers as the adhesive layer 31 and the resin layer 32 are used as the adhesive layer 35 and the resin layer 36, the thermal expansion coefficient of the resin layer 36 can be set to $1/10$ or less of the thermal expansion coefficient of the adhesive layer 35.

In an endoscope 1 on which the imaging module 40B having the above-mentioned structure is mounted, the thermal expansion coefficient of the resin layer 36 is set to $1/10$ or less of the thermal expansion coefficient of the adhesive layer 35. For this reason, the thermal expansion of the resin layer 36 can be prevented under a high temperature environment. As a result, it is possible to enhance the reliability of a product by preventing the separation of the adhesive layer 35.

In a case in which the elastic modulus of the resin layer 32 is lower than the elastic modulus of the adhesive layer 31 even though a difference between the thermal expansion coefficient of the adhesive layer 31 and the thermal expansion coefficient of the resin layer 32 is not large, the separation of the adhesive layer 31 can be prevented in the imaging module 40 of FIG. 2.

From the examination of various materials that could be used for the resin layer and the adhesive layer, it was found that the elastic modulus of the resin layer 32 could be set to $1/10$ or less of the elastic modulus of the adhesive layer 31 in a case in which an adhesive (silicon resin-based adhesive) containing a silicon resin as a main component was used as the resin layer 32 and an adhesive (epoxy resin-based adhesive) containing an epoxy resin as a main component was used as the adhesive layer 31. Further, according to the combination of these adhesives, it was found that the separation of the adhesive layer 31 could be sufficiently prevented. The main component of an element of this specification means a component having the highest content among materials of the element except for water or a solvent.

Even in the imaging module 40A of FIG. 4, likewise, in a case in which the elastic modulus of the resin layer 34 is set to be lower than the elastic modulus of the adhesive layer 33 (preferably $1/10$ or less of the elastic modulus of the adhesive layer 33), it is possible to enhance the reliability of a product by preventing the separation of the adhesive layer 33 even though a resin layer and an adhesive layer having a difference in thermal expansion coefficient, which is not too large, are used as the resin layer 34 and the adhesive layer 33.

Even in the imaging module 40B of FIG. 5, likewise, in a case in which the elastic modulus of the resin layer 36 is set to be lower than the elastic modulus of the adhesive layer 35 (preferably $1/10$ or less of the elastic modulus of the adhesive layer 35), it is possible to enhance the reliability of a product by preventing the separation of the adhesive layer 35 even though a resin layer and an adhesive layer having a difference in thermal expansion coefficient, which is not too large, are used as the resin layer 36 and the adhesive layer 35.

The followings will be disclosed in this specification as described above.

(1) An endoscope comprising:

an insertion part that is to be inserted into a subject;

a first unit that is built in a distal end portion of the insertion part and includes a first optical member;

a second unit that is built in the distal end portion of the insertion part and includes a second optical member;

an adhesive layer that is formed between a light transmission surface of the first optical member and a light transmission surface of the second optical member and adheres the first optical member to the second optical member; and a resin layer that fills a gap larger than a thickness of the adhesive layer formed between the first unit and the second unit, in which a thermal expansion coefficient of the resin layer is set to $1/10$ or less of a thermal expansion coefficient of the adhesive layer.

(2) The endoscope according to (1), in which a thickness of the resin layer is 100 or more times the thickness of the adhesive layer.

(3) The endoscope according to (1) or (2), in which a value, which is obtained by multiplying the thermal expansion coefficient of the adhesive layer and the thickness of the adhesive layer, is equal to or larger than a value that is obtained by multiplying the thermal expansion coefficient of the resin layer and the thickness of the resin layer.

(4) The endoscope according to any one of (1) to (3), in which each of the light transmission surface of the first optical member and the light transmission surface of the second optical member is a flat surface.

(5) The endoscope according to (4), in which the first optical member is a prism, and the second optical member is a cover glass of an imaging element.

(6) The endoscope according to (4), in which the first optical member is an imaging lens, and the second optical member is a prism.

(7) The endoscope according to (4), in which the first optical member is an imaging lens, and the second optical member is a cover glass of an imaging element.

(8) An endoscope comprising:

an insertion part that is to be inserted into a subject;

a first unit that is built in a distal end portion of the insertion part and includes a first optical member;

a second unit that is built in the distal end portion of the insertion part and includes a second optical member;

an adhesive layer that is formed between a light transmission surface of the first optical member and a light transmission surface of the second optical member and adheres the first optical member to the second optical member; and a resin layer that fills a gap larger than a thickness of the adhesive layer formed between the first unit and the second unit, in which an elastic modulus of the resin layer is set to be smaller than an elastic modulus of the adhesive layer.

(9) The endoscope according to (8), in which the elastic modulus of the resin layer is set to $1/10$ or less of the elastic modulus of the adhesive layer.

(10) The endoscope according to (8) or (9),
in which the adhesive layer is formed of an epoxy resin-based adhesive, and
the resin layer is formed of a silicon resin-based adhesive.

(11) An endoscope apparatus comprising:
the endoscope according to any one of (1) to (10);
a light source device to which the endoscope is connected; and
a control device to which the endoscope is connected and which controls the endoscope and the light source device.

EXPLANATION OF REFERENCES

100: endoscope apparatus
1: endoscope
2: body section
3: display unit
4: control device
5: light source device
6: input unit
10: insertion part
10A: soft portion
10B: bendable portion
10C: distal end portion
11: operation box
12: angle knob
13: universal cord
31, 33, 35: adhesive layer
32, 34, 36: resin layer
32a, 34a, 36a: gap
40, 40A, 40B: imaging module
41: lens barrel
42: prism holder
42A: lens holder
43: first lens
44: second lens
45: third lens
46: fourth lens
47: fifth lens
48: prism
48a: light incident surface
48b: inclined surface
48c: light-emitting surface
50, 70: semiconductor chip
51, 71: imaging element
51a, 71a: imaging surface
52, 72: spacer
53, 73: cover glass
53a: surface
60: flexible board
60a: one end portion
60b: opening portion
60c: bent portion
60d: straight portion
60e: the other end portion
60f: branch portion
60g: sub-board
61: cover
62: soldering portion
70a: board
80: signal cable
81: signal line
U1, U3, U5: first unit
U2, U4, U6: second unit

What is claimed is:

1. An endoscope comprising:
an insertion part that is to be inserted into a subject;
a first unit that is built in a distal end portion of the insertion part and includes a first optical member and an optical member holder, wherein the first optical member is in contact with a proximal end portion of the optical member holder;
a second unit that is built in the distal end portion of the insertion part and includes a second optical member;
an adhesive layer that is formed between a light transmission surface of the first optical member and a light transmission surface of the second optical member and adheres the first optical member to the second optical member; and
a resin layer that fills a gap larger than a thickness of the adhesive layer formed between the first unit and the second unit,
wherein a thermal expansion coefficient of the resin layer is set to $1/10$ or less of a thermal expansion coefficient of the adhesive layer,
wherein the first optical member is a prism, and
the second optical member is a cover glass of an imaging element.

2. The endoscope according to claim 1,
wherein a thickness of the resin layer is 100 or more times the thickness of the adhesive layer.

3. The endoscope according to claim 2,
wherein a value, which is obtained by multiplying the thermal expansion coefficient of the adhesive layer and the thickness of the adhesive layer, is equal to or larger than a value that is obtained by multiplying the thermal expansion coefficient of the resin layer and the thickness of the resin layer.

4. The endoscope according to claim 2,
wherein each of the light transmission surface of the first optical member and the light transmission surface of the second optical member is a flat surface.

5. The endoscope according to claim 1,
wherein a value, which is obtained by multiplying the thermal expansion coefficient of the adhesive layer and the thickness of the adhesive layer, is equal to or larger than a value that is obtained by multiplying the thermal expansion coefficient of the resin layer and the thickness of the resin layer.

6. The endoscope according to claim 5,
wherein each of the light transmission surface of the first optical member and the light transmission surface of the second optical member is a flat surface.

7. The endoscope according to claim 1,
wherein each of the light transmission surface of the first optical member and the light transmission surface of the second optical member is a flat surface.

8. An endoscope comprising:
an insertion part that is to be inserted into a subject;
a first unit that is built in a distal end portion of the insertion part and includes a first optical member and an optical member holder, wherein the first optical member is in contact with a proximal end portion of the optical member holder;
a second unit that is built in the distal end portion of the insertion part and includes a second optical member;
an adhesive layer that is formed between a light transmission surface of the first optical member and a light transmission surface of the second optical member and adheres the first optical member to the second optical member; and a resin layer that fills a gap larger than a thickness of the adhesive layer formed between the first unit and the second unit,
wherein an elastic modulus of the resin layer is set to be smaller than an elastic modulus of the adhesive layer,
wherein the first optical member is a prism, and
the second optical member is a cover glass of an imaging element.

9. The endoscope according to claim 8,
wherein the elastic modulus of the resin layer is set to 1/10 or less of the elastic modulus of the adhesive layer.

10. The endoscope according to claim 9,
wherein the adhesive layer is formed of an epoxy resin-based adhesive, and
the resin layer is formed of a silicon resin-based adhesive.

11. The endoscope according to claim 8,
wherein the adhesive layer is formed of an epoxy resin-based adhesive, and
the resin layer is formed of a silicon resin-based adhesive.

12. An endoscope apparatus comprising:
the endoscope according to claim 1;
a light source device to which the endoscope is connected; and
a control device to which the endoscope is connected and which controls the endoscope and the light source device.

13. An endoscope apparatus comprising:
the endoscope according to claim 2;
a light source device to which the endoscope is connected; and
a control device to which the endoscope is connected and which controls the endoscope and the light source device.

14. An endoscope apparatus comprising:
the endoscope according to claim 5;
a light source device to which the endoscope is connected; and
a control device to which the endoscope is connected and which controls the endoscope and the light source device.

15. An endoscope apparatus comprising:
the endoscope according to claim 3;
a light source device to which the endoscope is connected; and
a control device to which the endoscope is connected and which controls the endoscope and the light source device.

16. An endoscope apparatus comprising:
the endoscope according to claim 7;
a light source device to which the endoscope is connected; and
a control device to which the endoscope is connected and which controls the endoscope and the light source device.

17. An endoscope apparatus comprising:
the endoscope according to claim 4;
a light source device to which the endoscope is connected; and
a control device to which the endoscope is connected and which controls the endoscope and the light source device.

* * * * *